United States Patent [19]

Gündermann et al.

[11] 4,302,537
[45] Nov. 24, 1981

[54] REAGENT AND METHOD FOR THE DETERMINATION OF PEROXIDASE

[75] Inventors: Karl-Dietrich Gündermann, Clausthal-Zellefeld; Karl Wulff, Weilheim; Fritz Stachler, Tutzing; Hans-Ralf Linke, Raisting, all of Fed. Rep. of Germany

[73] Assignee: Boehringer Mannheim GmbH, Mannheim-Waldhof, Fed. Rep. of Germany

[21] Appl. No.: 120,191

[22] Filed: Feb. 11, 1980

[30] Foreign Application Priority Data

Feb. 21, 1979 [DE] Fed. Rep. of Germany ....... 2906732

[51] Int. Cl.³ .............................................. C12Q 1/66
[52] U.S. Cl. ..................................... 435/7; 23/230 B; 252/408; 260/326 C; 435/28
[58] Field of Search .................. 435/7, 28; 23/230 B; 260/326 C; 252/408

[56] References Cited

U.S. PATENT DOCUMENTS 3,654,179  4/1972  Bauer ................................. 435/28
3,986,833  10/1976  Mast et al. ....................... 435/28 X

*Primary Examiner*—Robert J. Warden

*Attorney, Agent, or Firm*—Sprung, Felfe, Horn, Lynch & Kramer

[57] ABSTRACT

The present invention provides a method for the determination of peroxidase in the presence of a compound, the enzyme-catalysed oxidation of which with a peroxy compound results in the emission of light, which is measured, wherein 7-dimethylaminonaphthalene-1,2-dicarboxylic acid hydrazide of the formula

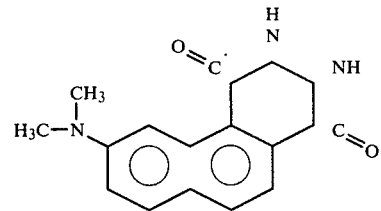

is used as light-emitting compound.

The present invention also provides a reagent for the determination of peroxidase, comprising 7-dimethylaminonaphthalene-1,2-dicarboxylic acid hydrazide, a system providing hydrogen peroxide and a buffer substance of pH 6 to 9.

20 Claims, 3 Drawing Figures

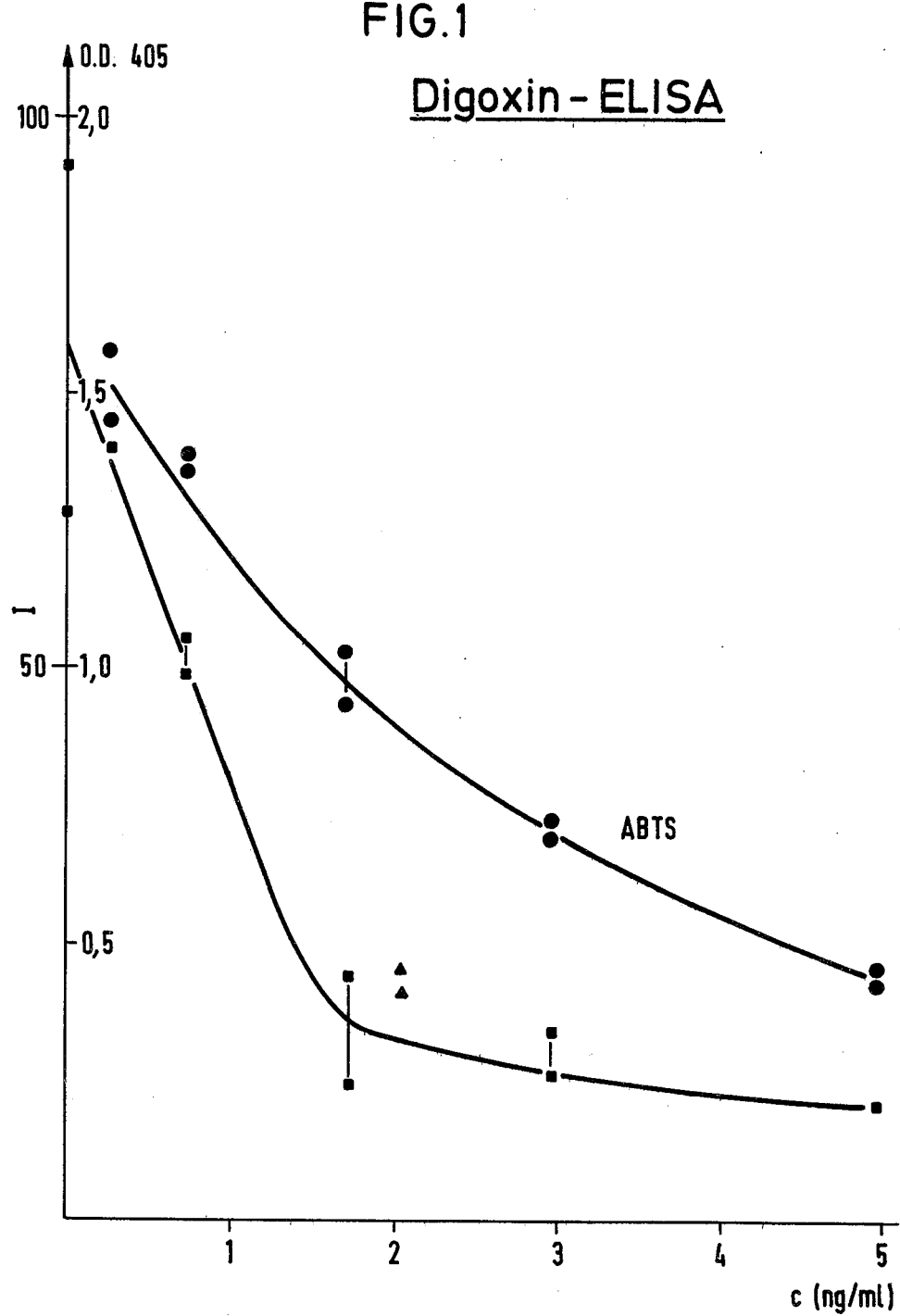

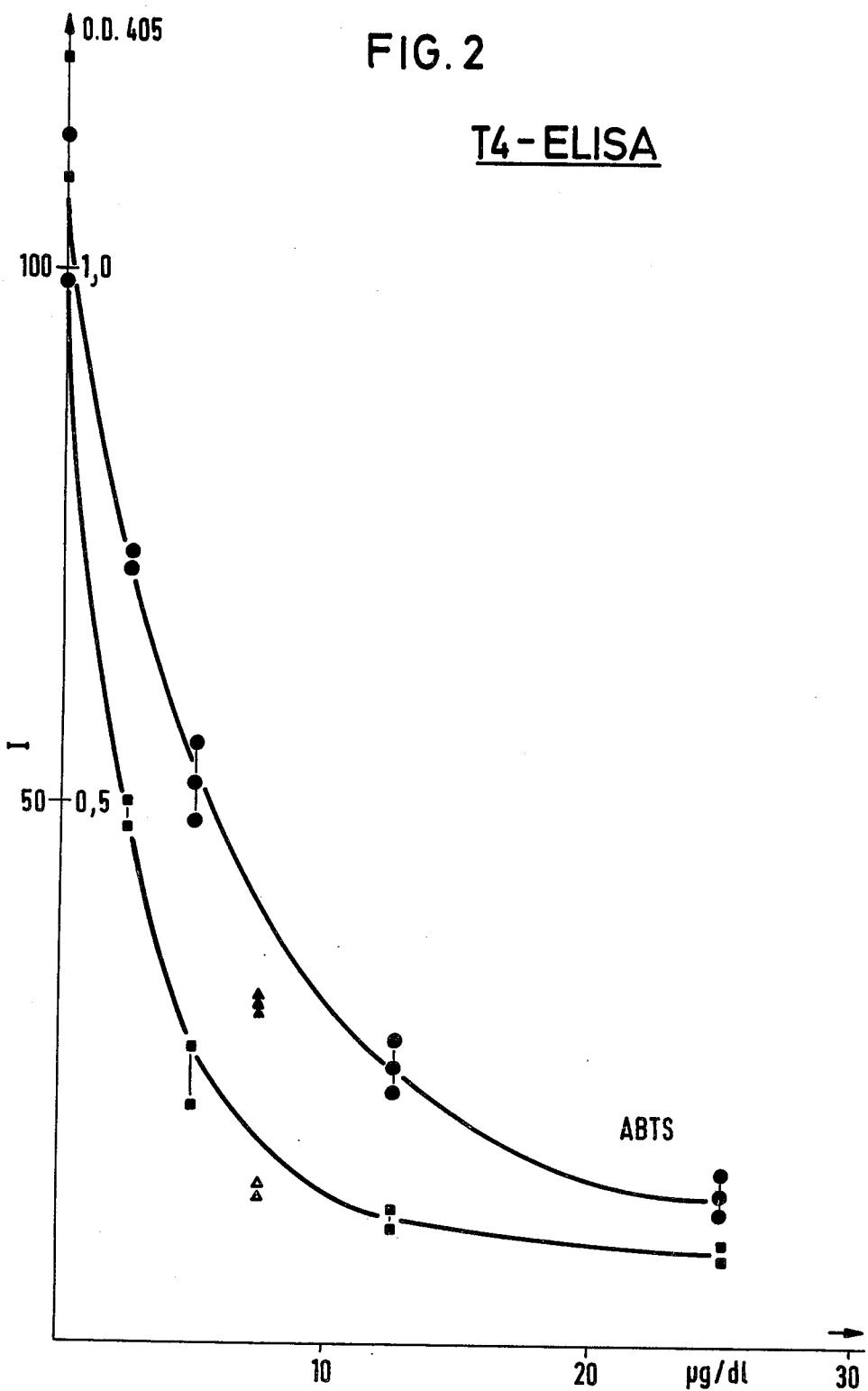

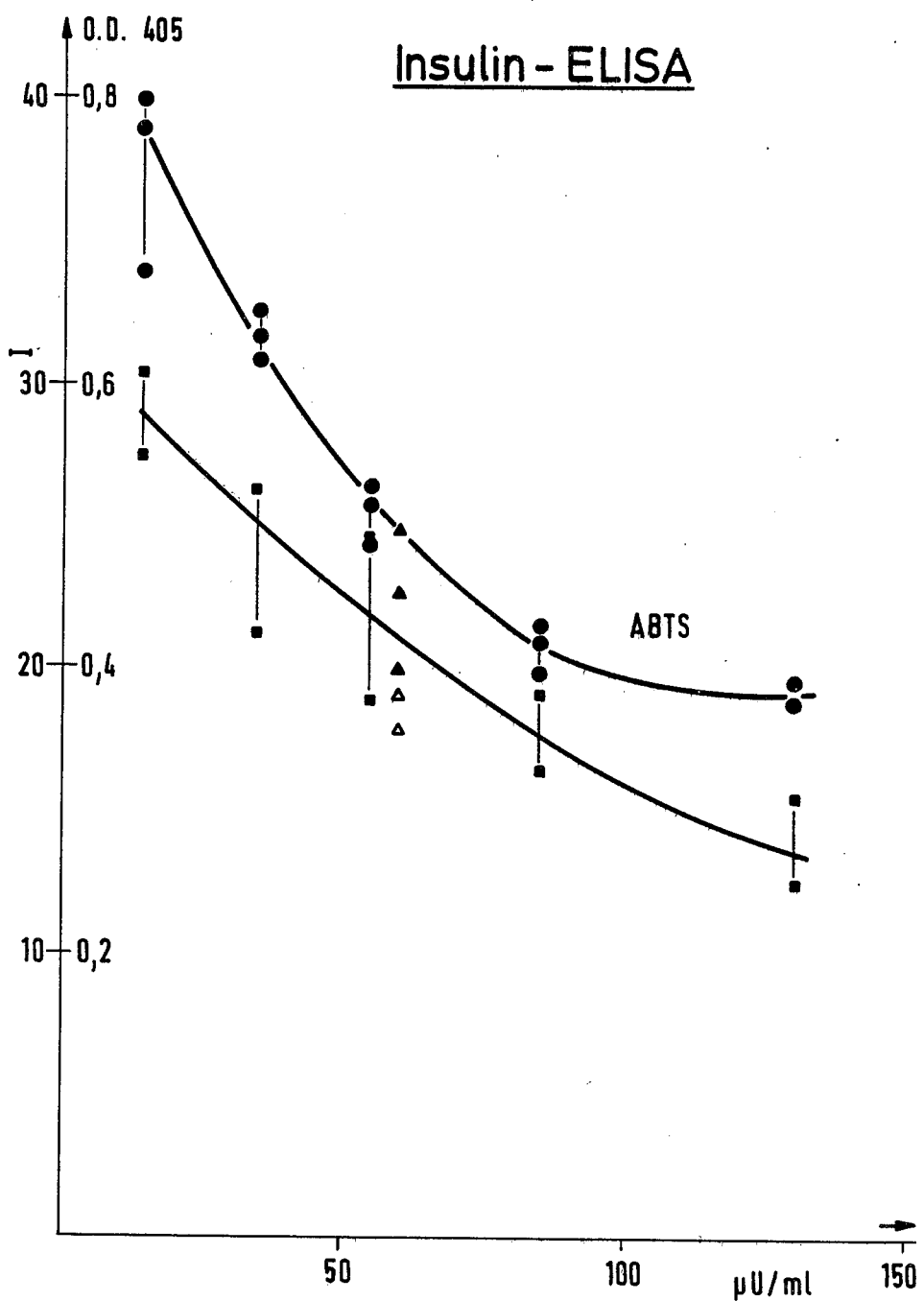

REAGENT AND METHOD FOR THE DETERMINATION OF PEROXIDASE

This invention relates to a reagent and method for the determination of peroxidase.

Peroxidase (POD; donor: hydrogen peroxidase oxidoreductase, EC 1.11.17) designates a group of enzymes which catalyze the dehydrogenation of a large group of organic compounds. The determination of POD is of special importance in conjunction with preceding reactions in which hydrogen peroxide is formed, for example for the determination of blood sugar, as well as in enzyme-immunological determinations which employ POD as a marker enzyme. Other analytical methods in which the determination of POD is of importance include, for example, the determination of galactose, hydrogen peroxide, catalase and oxidases.

It is known to measure POD by the decrease of the hydrogen peroxide or of the hydrogen donor, as well as by the formation of the dehydrogenated compound. The latter method has achieved particular importance, the substrate thereby subjected to dehydrogenation being, for example, di-o-anisidine, guaiacol or (2,2'-azino-di-(3-ethylbenzthiazoline-6-sulphonic acid).

These known methods have admittedly proved to be useful but there is, nevertheless, a need for methods of higher sensitivity which are, in particular, suitable for considerably shortening the time needed for a POD determination in the scope of enzyme immune tests. As already mentioned, POD plays an important part as marker enzyme in the so-called "enzyme-immuno assays" (ELISA tests), numerous test reagents depending upon this system being commercially available. In the case of these reagents or processes, the actual POD determination with, for example, ABTS as substrate, takes about 60 minutes. A considerable reduction of this time requirement is, therefore, desirable.

Published Federal Republic of Germany Patent Application No. 28 11 228 describes a process for the determination of POD in the presence of a phenolic compound which, upon enzyme-catalyzed oxidation thereof with hydrogen peroxide and hydrogen peroxide-containing compounds, emits light, this emitted light being measured. Pyrogallol is thereby used as the phenolic compound. The use of this process admittedly makes it possible to achieve an increase of the sensitivity but the quantum yield still leaves something to be desired. The same also applies to luminol, the use of which has also already been suggested for the same purpose.

Therefore, it is an object of the present invention to provide a process for the determination of the activity of peroxidase with the help of a chemiluminescent reaction which provides a better quantum yield than the hitherto known processes of this kind and enables the sensitivity of the POD determination to be substantially improved and the period of time of the POD determination in the ambit of an enzyme-immuno assay to be considerably shortened.

The present invention provides a reagent and a method for the determination of peroxidase in the presence of a compound, the enzyme-catalyzed oxidation of which, with a peroxy compound, results in the emission of light, which is measured, wherein 7-dimethylaminonaphthalene-1,2-dicarboxylic acid hydrazide of the formula

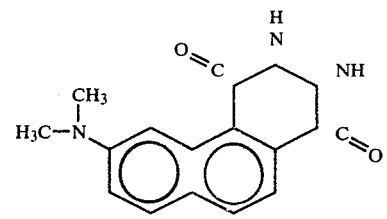

is used as light-emitting compound.

BRIEF DESCRIPTION OF THE DRAWINGS

In the drawings:

FIG. 1 is a calibration curve with the amount of digoxin plotted against emitted light and in comparison with the known ABTS method.

FIG. 2 is a calibration curve similar to FIG. 1 for Thyroxin ($T_4$).

FIG. 3 is a calibration curve similar to FIG. 1 for Insulin.

The present invention is based upon the surprising ascertainment that 7-dimethylaminonaphthalene-1,2-dicarboxylic acid hydrazide, upon POD-catalyzed oxidation thereof by peroxy compounds, gives a quantum yield increased by a multiple in comparison with the luminescent substrates previously used for this purpose.

Besides the determination of peroxidase itself, this process is of special importance in the scope of enzyme-immuno assays which employ POD as a marking enzyme. In the case of this preferred embodiment of the process according to the present invention, the POD determination is carried out in the scope of an immunological haptene determination in which a known amount of a POD-marked haptene is added to the sample to be investigated which contains an unknown amount of the haptene, the sample is then contacted with a specific antibody of the haptene bound to a solid carrier, the liquid phase is separated from the solid phase and the POD activity (ELISA test) measured in one of the two phases.

For the explanation of the present invention, in the following, such as ELISA test is described using, as an example, a commercially available test for the determination of digoxin concentrations in blood serum. The inner surface of a test tube is loaded with specific antibodies against digoxin, the antibodies thereby being so firmly bound covalently or adsorptively on the wall of the test tube that they cannot be washed away. When a digoxin solution is placed into such a reaction vessel, then the digoxin is bound by the carrier-bound antibodies. If a POD-labeled digoxin is used, then, after washing out the excess of POD-labeled digoxin molecules remaining in the solution, the amount of the POD-labeled digoxin molecules bound to the wall of the vessel by means of the antibodies or the amount thereof remaining in the solution can be determined quantitatively by measurement of the POD activity.

If, now, it is desired to determine an unknown concentration of digoxin in a sample, then an aliquot of this sample, together with a known amount of POD-labeled digoxin, is placed in the reaction vessel. The labeled and the unlabeled digoxin molecules compete for the binding places and an equilibrium is obtained. The more unlabeled digoxin is introduced into the reaction vessel with the sample, then the less labeled digoxin is bound to the wall of the vessel. With the help of a calibration curve, the amount of digoxin in the sample solution can, therefore, be determined by measurement of the POD.

Examples of other haptenes which can be assayed by this method include thyroxin (T4) and insulin.

In the case of the commercially available ELISA tests, the activity of the POD is frequently determined photometrically with the use of ABTS as chromogenic substrate. The lower sensitivity limit of this process is 1 ng./ml. of test volume. Therefore, this process is admittedly more sensitive than the previously known methods using a chemiluminescent reaction. Nevertheless, the photometric ABTS method requires an incubation time of 60 minutes for the color development.

With the process according to the present invention, it is possible to shorten the assay time essentially for the enzyme activity determination in such an ELISA test from 60 minutes to 2 to 3 minutes, with the same or even better sensitivity. The assay is preferably carried out by measuring the amount of light emitted in a definite interval of time.

The process according to the present invention is preferably carried out at a pH of from 6 to 9 and more preferably of from 7.5 to 8.5.

The buffer used is preferably a potassium phosphate buffer or a glycine-sodium hydroxide buffer, although other buffers, for example tris hydrochloric acid, tris sulphate and tris acetate, can also be used. The preferred buffer concentration is 10 to 1000 mMol/liter.

The chromogenic substrate employed according to the present invention is preferably employed in an amount of from 0.1 μMol to 100 μMol/liter.

The determination process according to the present invention can be carried out at the temperature usually employed for enzymatic determinations, i.e. from about 20° to 37° C., the temperature range of from 22° to 30° C. being especially preferred.

The present invention also provides a reagent for the determination of POD which comprises 7-dimethylaminonaphthalene-1,2-dicarboxylic acid hydrazide, a hydrogen peroxide donor and a buffer substance of pH 6 to 9.

According to a preferred embodiment of the present invention, this reagent comprises 0.1 to 100 μMol/liter 7-dimethylaminonaphthalene-1,2-dicarboxylic acid hydrazide, 50 to 500 mMol/liter potassium phosphate or glycine buffer, 10 to 200 μMol/liter hydrogen peroxide and optionally 0.01 to 1 mMol/liter of a sequestering agent.

The sequestering agent which is optionally used can be any substance known for this purpose, for example, ethylenediamine-tetraacetic acid (EDTA) and the like.

Furthermore, the reagent can contain conventional stabilization agents, for example serum albumen, carbohydrates and the like.

The hydrogen peroxide donor used according to the present invention can be hydrogen peroxide per se or a system providing hydrogen peroxide, such as a known substance which liberates hydrogen peroxide, for example urea perhydrate ("solid hydrogen peroxide") or the like, or an organic hydroperoxide in which one of the hydrogen atoms of hydrogen peroxide is replaced by an organic radical. Solid salts of hydrogen peroxide, for example sodium peroxide, which, upon dissolving in water, behave like a mixture of hydrogen peroxide and the corresponding hydroxyl compound, can also be employed. Thus, for example, use can be made of a combination of glycine and sodium peroxide which, upon dissolving in water, forms a glycine-sodium hydroxide buffer, as well as hydrogen peroxide.

Apart from the above-mentioned components, the reagent according to the present invention preferably also contains a haptene marked with POD, as well as a carrier-bound, specific antibody against the haptene in question when the reagent is to be used in an enzyme-immune test. Furthermore, other components which are conventional in such ELISA reagents can also be present, for example, further buffers, stabilizing agents and the like.

The following Examples are given for the purpose of illustrating the present invention:

EXAMPLE 1

A commercially-available enzyme-immunological in vitro test for the quantitative determination of digoxin according to the ELISA principle (Enz-Immun-Test, Boehringer Mannheim GmbH) was carried out as follows:

In a plastic test tube, coated on the inside with about 60 pg. digoxin antibodies, were mixed 1.0 ml. of a solution of POD-marked digoxin (about 12 U/liter POD) in phosphate buffer (40 mMol/liter, pH 6.8), which contained 0.25% by weight bovine serum albumen, as well as 0.1 ml. serum as sample, and left to stand for 1 hour at ambient temperature (20° to 25° C.). After termination of this incubation period, the contents of the test tube were sucked out and discarded and the test tube was rinsed out once with cooled tap water. Into the test tube there was then introduced 1 ml. of a solution of 100 μMol/liter 7-dimethylaminonaphthalene-1,2-dicarboxylic acid hydrazide in 100 mMol/liter potassium phosphate buffer (pH 8.2), which contained 0.1 mMol/liter EDTA. The reaction was then initiated by the addition of 120 μMol/liter hydrogen peroxide (end concentration). In a photometer (ATP-Photometer of the firm SAI, San Diego, Calif., U.S.), there was then measured the emitted light between the 2nd and the 5th minute after the initiation. The signal recorded on the recording device was integrated. From a calibration curve, which was obtained in an analogous manner by the use of known amounts of digoxin, there was determined the amount of digoxin corresponding to the measured light signal.

In FIG. 1 of the accompanying drawings, there is shown the calibration curve, illustrated as the amount of digoxin against the emitted amount of light, in comparison with the previously known photometric process using the color reaction with ABTS, the curve giving the ratio of the amount of digoxin to the extinction at a wavelength of Hg 405 nm.

EXAMPLE 2

In a manner analogous to that described in Example 1, the enzyme-immunological determination of thyroxin (T4) was carried out according to the ELISA principle, with the use of a commercially available test (Boehringer Mannheim GmbH). In this case, for the incubation there was used 1 ml. of a solution which contains POD-marked T4 (about 12 U/liter POD) in phosphate buffer (17.8 mMol/liter, pH 8.6), which contained 120 mMol/liter barbiturate and 0.20% bovine serum albumen. The amount of serum was 0.02 ml.

After incubating for 2 hours at ambient temperature (20° to 25° C.), the contents of the test tube were, as described in Example 1, sucked out and the test tube was washed out with tap water. There was then added thereto the same solution as described in Example 1 and the evaluation also carried out in the same manner. FIG. 2 of the accompanying drawings shows graphically the calibration curve obtained in the described manner with the use of a standard serum with differing dilutions, in comparison with a curve obtained according to the known process with the use of ABTS as chromogenic substrate.

EXAMPLE 3

In a manner analogous to that described in Example 1, with the use of a commercially available enzyme-immunological test according to the ELISA principle (Insulin-ELISA of Boehringer Mannheim GmbH), the immunological reaction was carried out in plastic test tubes coated with antibodies against insulin (insulin-binding capacity 6 to 10 μU/test tube). 0.2 ml. Serum as sample were incubated in the prescribed manner with 1.0 ml. of a solution of POD-marked insulin (about 15 U/liter POD) in phosphate buffer (40 mMol/liter, pH 6.8), which contained 0.25% bovine serum albumen. Subsequently, the liquid phase was discarded, the test tube was rinsed out with cold water and the determination of the POD bound to the test tube wall carried out as described in Example 1 with the use of the same reagent solution. FIG. 3 of the accompanying drawings shows the calibration curve obtained in this manner, in comparison with a calibration curve obtained with the use of ABTS as chromogenic substrate.

It will be understood that the specification and examples are illustrative but not limitative of the present invention and that other embodiments within the spirit and scope of the invention will suggest themselves to those skilled in the art.

What is claimed is:

1. Method for the determination of peroxidase in a sample, which method comprises contacting the sample with a peroxy compound selected from hydrogen peroxide or an organic hydroperoxide and 7-dimethylaminonaphthaline-1,2-dicarboxylic acid hydrozine of the formula

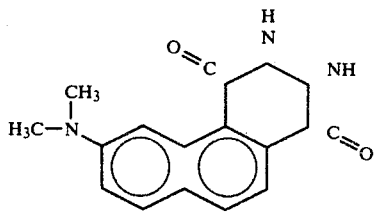

and measuring the emission of light as a measure of the peroxidase initially present in the sample.

2. Method as claimed in claim 1 for the determination of haptene by way of a peroxidase determination, which process comprises before the step of adding said acid hydrazide to said test sample, adding a known amount of peroxide marked haptene to a sample containing an unknown amount of haptene, contacting the sample with a specific anti-body of the haptene bound to a solid carrier, separating the solid phase from the liquid phase, and selecting one of said solid phase or said liquid phase as said test sample.

3. Method as claimed in claim 1 wherein the amount of light emitted in a definite interval of time is measured.

4. Method as claimed in claim 1 carried out at a pH of 6 to 9.

5. Method as claimed in claim 4 carried out at a pH of 7.5 to 8.5.

6. Method as claimed in claim 4 wherein the pH is adjusted with a buffer substance with a concentration of 10 to 1000 mMol/liter.

7. Method as claimed in claim 1 wherein a potassium phosphate or glycine buffer means is used.

8. Method as claimed in claim 1 wherein the step of contacting the sample with the acid hydrazide further comprises simultaneously contacting the acid hydrazide with 10 to 200 μMol/liter of hydrogen peroxide.

9. Method as claimed in claim 1 wherein 0.1 to 100 μMol/liter 7-dimethylaminonaphthalene-1,2-dicarboxylic acid hydrazide are used.

10. Method as claimed in claim 1 carried out at a temperature of from about 20° to 37° C.

11. Method as claimed in claim 10 carried out at a temperature of from 22° to 30° C.

12. Reagent for the determination of peroxidase comprising 7-dimethylaminonaphthalene-1,2-dicarboxylic acid hydrazide, a system providing hydrogen peroxide and a buffer substance of pH 6 to 9.

13. Reagent as claimed in claim 12 which comprises
    0.1 to 100 μMol/liter 7-dimethylaminonaphthalene-1,2-dicarboxylic acid hydrazide;
    50 to 500 mMol/liter potassium phosphate or glycine buffer; and
    10 to 200 μMol/liter hydrogen peroxide.

14. Reagent as claimed in claim 13 additionally containing 0.01 to 1 mMol per liter of a sequestering agent.

15. Reagent as claimed in claim 14 wherein the sequestering agent is ethylenediaminetetraacetic acid.

16. Reagent as claimed in claim 12 additionally comprising a haptene marked with peroxidase and carrier-bound specific antibodies against the haptene.

17. Reagent as claimed in claim 12 additionally comprising a stabilizing agent.

18. Reagent as claimed in claim 17 wherein said stabilizing agent is serum albumen or a carbohydrate.

19. Reagent as claimed in claim 12 wherein the system providing hydrogen peroxide is hydrogen peroxide or a substance which liberates hydrogen peroxide.

20. Reagent as claimed in claim 19 wherein the substance which liberates hydrogen peroxide is urea perhydrate, an organic hydroperoxide or a solid salt of hydrogen peroxide.

* * * * *